(12) United States Patent
Akaza et al.

(10) Patent No.: US 8,992,947 B2
(45) Date of Patent: Mar. 31, 2015

(54) METHOD FOR PREDICTING THERAPEUTIC EFFECT OF CHEMOTHERAPY ON RENAL CELL CANCER

(75) Inventors: Hideyuki Akaza, Tokyo (JP); Seiji Naito, Fukuoka (JP); Toshinori Oka, Tokushima (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/264,811

(22) PCT Filed: Apr. 22, 2010

(86) PCT No.: PCT/JP2010/057176
§ 371 (c)(1),
(2), (4) Date: Dec. 23, 2011

(87) PCT Pub. No.: WO2010/123078
PCT Pub. Date: Oct. 28, 2010

(65) Prior Publication Data
US 2012/0101102 A1    Apr. 26, 2012

(30) Foreign Application Priority Data

Apr. 22, 2009   (JP) ................ 2009-104189

(51) Int. Cl.
| | | |
|---|---|---|
| A61P 35/00 | (2006.01) | |
| A61K 31/513 | (2006.01) | |
| G01N 33/68 | (2006.01) | |
| C12Q 1/68 | (2006.01) | |
| G01N 33/574 | (2006.01) | |

(52) U.S. Cl.
CPC ........... *A61K 31/513* (2013.01); *A61K 2300/00* (2013.01); *C12N 2320/31* (2013.01); *G01N 33/57438* (2013.01); *G01N 2333/91017* (2013.01); *G01N 2800/52* (2013.01)
USPC ........................................ 424/400

(58) Field of Classification Search
None
See application file for complete search history.

(56) References Cited

U.S. PATENT DOCUMENTS 5,525,603 A    6/1996  Shirasaka et al.
2006/0116345 A1*  6/2006  Uchida et al. ........... 514/49

FOREIGN PATENT DOCUMENTS

WO   92/21345 A1   12/1992
WO   2004/081012 A1   9/2004

OTHER PUBLICATIONS

Rini et al. (Phase II Trial of Weekly Intravenous Gemcitabine With Continuous Infusion Fluorouracil in Patients With Metastatic Renal Cell Cancer, Jun. 2000, Journal of Clinical Oncology, vol. 18, pp. 2419-2426).*
Leichman et al (Quantification of intratumoral thymidylate synthase expression predicts for disseminated colorectal cancer response and resistance to protracted-infusion fluorouracil and weekly leucovorin, 1997, Journal of Clinical Oncology, vol. 15, pp. 3223-3229).*
Aschele et al (Thymidylate synthase protein expression in colorectal cancer metastases predicts for clinical outcome . . . , 2002, Annals of Oncology, vol. 13, pp. 1882-1892).*
Ikeda et al., "Ko Shuyozai 'TS-1' no Yakuri Sayo to Tainai Dotai", Antibiotics & Chemotherapy, vol. 17, No. 7, 2001, pp. 1318-1331.
"Ten'isei Jinsaibogan ni Taisuru S-1 no Koka to sono Koka Yosoku Inshi no Kento", The Journal of the Japan Society for Cancer Therapy, Sep. 14, 2009, vol. 44, No. 2, pp. 458.
Escudier et al., "Sorafenib in Advanced Clear-Cell Renal-Cell Carcinoma", The New England Journal of Medicine, Jan. 11, 2007, vol. 356, No. 2, pp. 125-134.
Ikeda et al., "Pharmacological Action and Disposition of Antitumor Agent TS-1", vol. 17, No. 7, 2001, pp. 106-119, 11 pages of English Abstract.
Motzer et al., "Systemic therapy for Renal Cell Carcinoma", The Journal of Urology, vol. 163, pp. 408-417, Feb. 2000.
Motzer et al., "Activity of SU11248, a Multitargeted Inhibitor of Vascular Endothelial Growth Factor Receptor and Platelet-Derived Growth Factor Receptor . . .", Journal of Clinical Oncology, vol. 24, No. 1, Jan. 1, 2006, pp. 16-24.
Motzer et al., "Sunitinib in Patients with Metastatic Renal Cell Carcinoma", JAMA.,Jun. 7, 2006, vol. 295, No. 21, pp. 2516-2524.
Yagoda et al., "Chemotherapy for Advanced Renal-Cell Carcinoma: 1983-1993", Seminars in Oncology, vol. 22, No. 1 Feb. 1995, pp. 42-60.

* cited by examiner

*Primary Examiner* — Brian-Yong Kwon
*Assistant Examiner* — Mark V Stevens
(74) *Attorney, Agent, or Firm* — Rothwell, Figg, Ernst & Manbeck, P.C.

(57) ABSTRACT

The present invention developed a novel antitumor agent for renal cell carcinoma that cannot be fully treated by the existing therapies. The present invention provides an antitumor agent comprising a combination drug of tegafur/gimeracil/oteracil potassium that ensures an excellent therapeutic effect in renal cell carcinoma patients that is superior to that of the existing therapies, by way of selecting the patients based on thymidylate synthase.

5 Claims, No Drawings

SEQUENCE LISTING

<160> NUMBER OF SEQ ID NOS: 6

<210> SEQ ID NO 1
<211> LENGTH: 22
<212> TYPE: DNA
<213> ORGANISM: Artificial
<220> FEATURE:
<223> OTHER INFORMATION: Forward Primer

<400> SEQUENCE: 1
gaatcacatc gagccactga aa                                              22

<210> SEQ ID NO 2
<211> LENGTH: 23
<212> TYPE: DNA
<213> ORGANISM: Artificial
<220> FEATURE:
<223> OTHER INFORMATION: Reverse Primer

<400> SEQUENCE: 2
gaagaatcct gagctttggg aaa                                             23

```
<210> SEQ ID NO 3
<211> LENGTH: 16
<212> TYPE: DNA
<213> ORGANISM: Artificial
<220> FEATURE:
<223> OTHER INFORMATION: Taqman Probe

<400> SEQUENCE: 3
cagcttcagc gagaac                                                   16

<210> SEQ ID NO 4
<211> LENGTH: 18
<212> TYPE: DNA
<213> ORGANISM: Artificial
<220> FEATURE:
<223> OTHER INFORMATION: Forward Primer

<400> SEQUENCE: 4
aaggccaacc gcgagaag                                                 18

<210> SEQ ID NO 5
<211> LENGTH: 21
<212> TYPE: DNA
<213> ORGANISM: Artificial
<220> FEATURE:
<223> OTHER INFORMATION: Reverse Primer

<400> SEQUENCE: 5
atagcaacgt acatggctgg g                                             21

<210> SEQ ID NO 6
<211> LENGTH: 15
<212> TYPE: DNA
<213> ORGANISM: Artificial
<220> FEATURE:
<223> OTHER INFORMATION: Taqman Probe

<400> SEQUENCE: 6
acccagatca tgttt                                                    15
```

METHOD FOR PREDICTING THERAPEUTIC EFFECT OF CHEMOTHERAPY ON RENAL CELL CANCER

CROSS REFERENCE TO RELATED APPLICATION

This application is a 35 U.S.C. 371 National Phase Entry Application from PCT/JP2010/057176, filed Apr. 22, 2010, which claims the benefit of Japanese Patent Application No. 2009-104189 filed on Apr. 22, 2009, the disclosure of which is incorporated herein in its entirety by reference.

TECHNICAL FIELD

The present invention relates to a method for predicting a therapeutic effect of chemotherapy with a combination drug of tegafur/gimeracil/oteracil potassium; and an antitumor agent to be administered to a patient who is likely to sufficiently respond to the chemotherapy. The present invention further relates to a method for treating renal cell carcinoma; and use of an antitumor agent comprising a combination drug of tegafur/gimeracil/oteracil potassium.

BACKGROUND ART

Among systemic therapies of renal cell carcinoma, only cytokine therapies using IFN-α and IL-2 had been found effective, though the effect was very small. However, since the molecular target drugs sorafenib and sunitinib were approved as therapeutic agents for renal cell carcinoma in Europe and the U.S., they have begun replace cytokine therapies as standard therapy of renal cell carcinoma.

However, Non-patent Literature 1 to 3 discloses that the clinical performance of those molecular target drugs (with respect to the patients in which cytokine therapies had no effect), namely, 10 to 36.5% response rate and 5.5 to 8.7 months median progression-free survival (PFS), are lower than in other cancers. Moreover, Japan has a poor record regarding practical accomplishment in medical care with molecular target drugs, and the effectiveness and the safety of molecular target drugs are not fully confirmed. Therefore, it is necessary to verify their effectiveness and safety.

In addition, in 1995, Yagoda et al. reported a general overview of the effectiveness of systematic therapies for renal cell carcinoma mainly using anticancer agents. Yagoda summarized 83 clinical test results, and disclosed that the response rate of the most effective agent, namely, 5-fluorouracil (5-FU) or floxuridine, was 13.4% (Non-patent Literature 4). In 1990s, studies mainly focused on floxuridine; however, no effect superior to that of cytokine therapies has thus far been confirmed (Non-patent Literature 5).

As such, a therapeutic system for renal cell carcinoma has not yet been established in Japan, and a standard therapy therefor has not yet been discovered. Further, even after manufacturing approval of the two molecular target drugs, patients have few treatment options, and the therapeutic circumstances of renal cell carcinoma patients are still not satisfactory.

CITATION LIST

Non-Patent Literature

[Non-patent Literature 1] N Engl J. Med. 2007; 356: 125-134
[Non-patent Literature 2] J Clin Oncol. 2006; 24: 16-24
[Non-patent Literature 3] JAMA. 2006; 295(21): 2516-2524
[Non-patent Literature 4] Semin Oncol. 1995; 22: 42-60
[Non-patent Literature 5] J Urol. 2000; 163: 408-417

SUMMARY OF INVENTION

Technical Problem

An object of the present invention is to provide a chemotherapy that ensures an excellent therapeutic effect in renal cell carcinoma patients. Another object of the present invention is to provide a method for treating renal cell carcinoma; and use of an antitumor agent comprising a combination drug of tegafur/gimeracil/oteracil potassium.

Solution to Problem

The inventors of the present invention conducted extensive research on chemotherapies for renal cell carcinoma, and found a method of predicting a patient who is likely to sufficiently respond to the chemotherapy with a combination drug of tegafur/gimeracil/oteracil potassium according to the expression level of thymidylate synthase gene (amount of mRNA or enzyme). With this finding, the inventors completed the present invention. The thymidylate synthase is hitherto known as a factor for defining the therapeutic effect of S-1 (a combination drug comprising tegafur/gimeracil/oteracil potassium at a molar ratio of 1:0.4:1) in treatments of other cancers (for example, Int. J. Cancer: 119, 1927-1933 (2006)); however, it was completely unknown that the amount of expression product (mRNA, enzyme) of thymidylate synthase gene can be used as an index for selecting the chemotherapy for the renal cell carcinoma patients.

Specifically, the present invention provides the following methods for predicting a therapeutic effect of chemotherapy with a combination drug of tegafur/gimeracil/oteracil potassium; and an antitumor agent. The present invention further provides the following method for treating renal cell carcinoma; and use of an antitumor agent comprising a combination drug of tegafur/gimeracil/oteracil potassium.

[Item 1]
A method for predicting a therapeutic effect of chemotherapy with a combination drug of tegafur/gimeracil/oteracil potassium with respect to renal cell carcinoma patients, the method comprising the steps of:

(1) measuring an expression level of thymidylate synthase gene in a biological sample, which is obtained from a patient and is likely to contain cancer cells; and (2) predicting that the patient is likely to sufficiently respond to the chemotherapy when the expression level measured in Step (1) is lower than a corresponding predetermined cut-off point.

[Item 2]
The method according to Item 1, wherein the molar ratio of respective active ingredients in the combination drug of tegafur/gimeracil/oteracil potassium, i.e., the ratio of tegafur:gimeracil:oteracil potassium, is 1:0.4:1.

[Item 3]
An antitumor agent comprising a combination drug of tegafur/gimeracil/oteracil potassium, characterized by performing the chemotherapy with respect to a cancer patient assumed to sufficiently respond to the chemotherapy in accordance with a result of the method of Item 1 or 2.

[Item 4]
A therapeutic method for gastric cancer, characterized by performing the combination chemotherapy with respect to a cancer patient assumed to sufficiently respond to the combination chemotherapy in accordance with a result of the method of Item 1 or 2.

[Item 5]

Use of an antitumor agent comprising a combination drug of tegafur/gimeracil/oteracil potassium to perform the combination chemotherapy with respect to a cancer patient assumed to sufficiently respond to the combination chemotherapy in accordance with a result of the method of Item 1 or 2.

Effect of Invention

The prediction method of the present invention enables selection of effective chemotherapy that ensures an excellent therapeutic effect (tumor shrinking effect, effect of prolonging progression free survival, etc.) in renal cell carcinoma patients. More specifically, the present invention makes it possible to accurately provide chemotherapy that has a superior therapeutic effect in renal cell carcinoma patients who are likely to highly respond to the chemotherapy, thereby allowing the patients to avoid unnecessary chemotherapies. Therefore, the present invention also has an advantage in terms of medical care expenses.

The present invention substantiated, for the first time, that the effectiveness of the above chemotherapy greatly depends on the expression level of thymidylate synthase gene, and that the chemotherapy is effective only in cases where the expression level of thymidylate synthase gene is equal to or less than a certain value.

DESCRIPTION OF EMBODIMENTS

The prediction method of the present invention predicts those patients who are likely to more strongly respond to chemotherapy with a combination drug of tegafur/gimeracil/oteracil potassium based on the expression level of thymidylate synthase gene in patients.

In the present invention, "sufficiently respond to the chemotherapy" indicates a condition in which a patient responds to the chemotherapy to a greater extent (in terms of tumor-shrinking effect, effect of prolonging progression-free survival, etc.) than that achieved with a standard therapy that is used both within the country and abroad (for example, molecular target drugs, sorafenib and sunitinib, etc.). Whether such a condition is shown can be determined by confirming whether the expression level of thymidylate synthase gene is equal to or less than a cut-off point. The expression level of thymidylate synthase gene that is equal to or less than a cut-off point is regarded as ensuring a sufficient therapeutic effect of the chemotherapy. The therapeutic effect in the present invention can be evaluated comprehensively by a tumor-shrinking effect, effect of prolonging progression-free survival, etc., each of which can be determined by the degree of tumor shrinkage, progression-free survival, etc.

The chemotherapy of the present invention for patients with renal cell carcinoma may be used alone for treatment without performing nephrectomy, and is preferably applicable to a type of chemotherapy that suppresses or treats metastasis or recurrence after partial or total extirpation of one kidney. For example, the method of the present invention can be applied to patients to whom cytokine therapy can be applied after nephrectomy, and patients with metastatic renal cell carcinoma who are judged to be ineligible for cytokine therapy. Specifically, therapeutic effects can be predicted both in cases where primary renal cell carcinoma is present before nephrectomy, and in cases where metastatic renal cell carcinoma is present after nephrectomy.

The antitumor agent of the present invention can be administered to a cancer patient assumed to sufficiently respond to the chemotherapy in accordance with a result of the method of the present invention, in cases where primary renal cell carcinoma is present before nephrectomy, in cases where metastatic renal cell carcinoma is present after nephrectomy, or further for the purpose of preventing recurrence of metastatic renal cell carcinoma after nephrectomy.

Tegafur (generic name, chemical name: 5-fluoro-1-(2-tetrahydrofuryl)-2,4-(1H,3H)-pyrimidinedione), an active ingredient in the present invention, is a known compound, and is a drug that is activated in vivo to release 5-fluorouracil, which is a substance responsible for the antitumor activity. Tegafur can be produced according to known methods such as, for example, the method disclosed in Japanese Examined Patent Publication No. S49-10510.

Gimeracil (generic name, chemical name: 2,4-dihydroxy-5-chloropyridine), an active ingredient in the present invention, is also a known compound. Although gimeracil itself does not exhibit any antitumor activity, it can inhibit metabolic inactivation of 5-fluorouracil in vivo, thereby potentiating the antitumor effect.

Oteracil potassium (generic name, chemical name: monopotassium 1,2,3,4-tetrahydro-2,4-dioxo-1,3,5-triazine-6-carboxylate), an active ingredient in the present invention, is also a known compound. Although oteracil potassium itself exhibits little antitumor activity, it is chiefly distributed in the gastrointestinal tract, where it inhibits the activation of 5-fluorouracil, thereby preventing gastrointestinal tract disorders.

The proportion of tegafur, gimeracil and oteracil potassium that are administered in the present invention is not particularly limited, as long as the purpose of each ingredient is achieved. For example, the proportion of tegafur, gimeracil and oteracil potassium may be within the same range as that in the known combination drug disclosed in U.S. Pat. No. 2,614,164. The proportion is usually such that, per mole of tegafur, gimeracil is used in a proportion of about 0.1 to about 5 moles and preferably about 0.2 to about 1.5 moles, and oteracil potassium is used in a proportion of about 0.1 to about 5 moles and preferably about 0.2 to about 2 moles. It is particularly preferred that the molar ratio of tegafur:gimeracil:oteracil potassium is 1:0.4:1.

The dose of each active ingredient in the present invention is suitably selected according to conditions such as dose regimen, age and sex of a patient, stage of disease, presence or absence of metastasis, medical history, and presence or absence of other antitumor agents. The pharmaceutical preparation of the present invention is preferably given in an amount using the following range as a standard: the amount of tegafur is about 0.1 to about 100 mg/kg/day, preferably about 0.2 to about 40 mg/kg/day, and more preferably about 0.5 to about 20 mg/kg/day; the amount of gimeracil is about 0.02 to about 30 mg/kg/day, preferably about 0.05 to about 12 mg/kg/day, and more preferably about 0.1 to about 6 mg/kg/day; and the amount of oteracil potassium is about 0.1 to about 100 mg/kg/day, preferably about 0.2 to about 40 mg/kg/day, and more preferably about 0.5 to about 20 mg/kg/day. Further, each active ingredient is administered in a single dose or multiple divided doses per day. The active ingredients are administered simultaneously or separately at intervals, and the order of administration thereof is not particularly limited.

In the present invention, tegafur, gimeracil, and oteracil potassium are provided as a combination drug that is formulated into one dosage form.

The dosage form of the preparation of the present invention is not particularly limited. Specific examples thereof include oral preparations (such as tablets, coated tablets, powders, granules, capsules, and fluids), injections, suppositories, patches, and ointments. When the active ingredients of the present invention are formulated into a plurality of dosage forms, the preparations may be presented in different dosage forms, or in the same dosage form. For example, the combination drug of tegafur/gimeracil/oteracil potassium is preferably prepared as an oral preparation.

The preparation of the present invention is produced using a pharmacologically acceptable carrier by formulation methods that are commonly known in each dosage form. Examples of the carrier include those that are widely used in common drugs, such as excipients, binders, disintegrators, lubricants, diluents, solubilizing agents, suspending agents, tonicity adjusting agents, pH adjusters, buffers, stabilizers, colorants, sweetening agents, flavoring agents, and soothing agents.

Examples of excipients include lactose, saccharose, sodium chloride, glucose, maltose, mannitol, erythritol, xylitol, maltitol, inositol, dextran, sorbitol, albumin, urea, starch, calcium carbonate, kaolin, crystalline cellulose, silicic acid, methylcellulose, glycerol, sodium alginate, gum arabic, mixtures thereof, and the like. Examples of lubricants include purified talc, stearic acid salts, borax, polyethylene glycol, mixtures thereof, and the like. Examples of binders include simple syrups, glucose solutions, starch solutions, gelatin solutions, polyvinyl alcohol, polyvinyl ether, polyvinylpyrrolidone, carboxymethylcellulose, shellac, methylcellulose, ethylcellulose, water, ethanol, potassium phosphate, mixtures thereof, and the like. Examples of disintegrators include dried starch, sodium alginate, powdered agar, powdered laminaran, sodium hydrogencarbonate, calcium carbonate, polyoxyethylene sorbitan fatty acid esters, sodium lauryl sulfate, stearic acid monoglycerides, starch, lactose, mixtures thereof, and the like. Examples of diluents include water, ethyl alcohol, macrogol, propylene glycol, ethoxylated isostearyl alcohol, polyoxylated isostearyl alcohol, polyoxyethylene sorbitan fatty acid esters, mixtures thereof, and the like. Examples of stabilizers include sodium pyrosulfite, ethylene diamine tetraacetic acid, thioglycolic acid, thiolactic acid, mixtures thereof, and the like. Examples of tonicity adjusting agents include sodium chloride, boric acid, glucose, glycerol, mixtures thereof, and the like. Examples of pH-adjusters and buffers include sodium citrate, citric acid, sodium acetate, sodium phosphate, mixtures thereof, and the like. Examples of soothing agents include procaine hydrochloride, lidocaine hydrochloride, mixtures thereof, and the like. Examples of solubilizing agents include polyethylene glycol, D-mannitol, and the like. Examples of suspending agents include stearyltriethanolamine, sodium lauryl sulfate, benzalkonium chloride, and the like. Examples of colorants include titanium oxide, iron oxide, and the like. Examples of sweetening/flavoring agents include saccharose, orange peel, citric acid, tartaric acid, and the like.

The administration schedule of the present invention is suitably selected according to conditions such as the age and sex of a patient, stage of disease, presence or absence of metastasis, and medical history. For example, the chemotherapy of the present invention is preferably conducted according to the following schedule. Tegafur, gimeracil and oteracil potassium are administered for 28 consecutive days followed by a 14-day withdrawal. This is regarded as one cycle, and one cycle or a plurality of cycles are conducted.

The target patients for the prediction method of the present invention are patients with renal cell carcinoma, and may also be patients with renal cell carcinoma as a primary focus and with renal cell carcinoma that has metastasized to an organ or tissue other than the kidney.

Biological samples that can be used in measuring the expression level of thymidylate synthase gene in the present invention are not particularly limited as long as they are likely to contain cancer cells. Examples thereof include body fluid (such as blood and urine), tissues, extracts thereof, and cultures of the obtained tissues. Methods for collecting biological samples can be suitably selected according to the type of biological samples or type of cancers. The preparation of DNA, RNA, and proteins from biological samples can be conducted according to commonly known methods. As the tissues, the kidney can be mentioned in particular; however, when cancer cells have metastasized from the kidney to other organs (for example, lung, bone, liver), lymph, peritoneum, or the like, the tissues at the metastasis sites become target tissues.

Thymidylate synthase is an enzyme that has an activity of synthesizing dTMP from dUMP using folic acid as a coenzyme, and is known as an enzyme required in DNA synthesis. Further, thymidylate synthase is known as a target enzyme of 5-fluorouracil. The base sequence and amino acid sequence of human thymidylate synthase gene are known (Nucleic Acids Res. 13:2035-2043 (1985)).

The prediction method of the present invention employs the expression level of thymidylate synthase gene as an index. The expression level may be that of mRNA, or that of a protein. Here, the expression level of mRNA can be measured using a probe or primer that specifically hybridizes with thymidylate synthase gene, according to known methods for measuring gene expression levels, such as Northern blotting method, quantitative or semi-quantitative PCR method (for example, RT-PCR method and real-time PCR method), and in situ hybridization method. The above expression level can be assessed by comparison with a protein/gene that is expressed at a constant level (for example, a housekeeping gene, such as (β-actin, or its expressed protein) as a reference standard.

The level of protein expression can be measured by conducting a known immunological assay, such as an enzyme immunoassay, radioimmunoassay, fluoroimmunoassay, ELISA, Western blotting technique, or immunohistochemical staining assay, using an antibody that specifically recognizes thymidylate synthase.

Probes used in the methods for measuring gene expression levels, such as Northern blot technique and in situ hybridization, are designed, according to commonly known probe design methods, to specifically hybridize with a continuous base sequence of at least 15 bases to the total base length, preferably 20 bases to the total base length, more preferably 30 bases to the total base length, of the base sequence of thymidylate synthase gene; and are in the form of polynucleotides having the above-mentioned base length.

Primers and probes used in quantitative or semi-quantitative PCR method, such as RT-PCR method and real-time PCR method, can be designed, for example, in the following manner.

The primers and probes of the present invention are designed according to commonly known primer and probe design methods, to specifically hybridize with a continuous base sequence of at least 10 bases to the total base length, preferably 10 to 100 bases, more preferably 10 to 50 bases, still more preferably 10 to 35 bases of the base sequence of thymidylate synthase gene; and are in the form of polynucleotides having the above-mentioned base length. For example, primers for detecting the expression products of thymidylate synthase gene, i.e., forward and reverse primers for PCR, can be designed and synthesized from exon regions of thymidylate synthase gene. The forward and reverse primers are designed such that one is designed based on the base sequence of the upstream region of exon regions of thymidylate synthase gene (forward primer), and the other is designed based on the base sequence of the downstream region of the exon regions (reverse primer). For example, in designing thymidylate synthase gene primers based on exons 1 to 3, when the forward primer is designed based on the sequence of the exon 1 region, the reverse primer is designed based on the sequence of the downstream exon 2 region or exon 3 region. The reverse primer is designed to be complementary to the sequence of mRNA of thymidylate synthase gene. Further, each primer can be made using the whole or a part of the base sequence of mRNA of thymidylate synthase gene containing the exon regions; however, it is desirable to design each primer in consideration of the efficiency of amplification from the exon regions in PCR.

Probes for detecting expression products of thymidylate synthase gene are not particularly limited as long as they can hybridize with a single-stranded DNA of thymidylate synthase gene that is to be amplified using the above primers by a PCR reaction. Any probes may be used as long as they have a sequence complementary to the base sequence of all exons of thymidylate synthase gene or a portion thereof, or as long as they are hybridizable under a stringent condition.

The probes are not always required to be fully complementary to the base sequence of thymidylate synthase gene as long as they specifically hybridize with thymidylate synthase gene. Such polynucleotides have an identity of not less than 70%, preferably not less than 80%, more preferably not less than 90%, still more preferably not less than 95%, and still further more preferably not less than 98%, in the base sequence, as compared to either the polynucleotide having a continuous base sequence of preferably at least 15 bases of the base sequence of thymidylate synthase gene, or the complementary polynucleotide thereof.

In the present invention, "specific hybridization" refers to a hybridization that forms a specific hybrid and does not form a nonspecific hybrid under a stringent hybridization condition. The stringent hybridization condition can be determined according to commonly known methods, for example, based on the melting temperature (Tm) of the nucleic acid at which the hybrid is formed. A specific cleaning condition to maintain the hybridization condition is commonly about "1×SSC, 0.1% SDS, 37° C.," more strictly about "0.5×SSC, 0.1% SDS, 42° C.," and still more strictly about "0.1×SSC, 0.1% SDS, 65° C."

Because the base sequence of thymidylate synthase gene in humans is known, the probes or primers can be made by commonly known synthesis methods, for example, using a commercially available nucleotide synthesizer, based on the base sequence. The probes or primers can also be prepared by PCR method using the base sequence as a template.

Moreover, to easily detect thymidylate synthase gene, the probes or primers may be labeled with a commonly used radioactive substance, fluorescent substance, chemical luminescent substance, or enzyme.

The antibody of the present invention is not particularly limited as long as it specifically recognizes thymidylate synthase. The antibody may be either monoclonal or polyclonal; or an antibody fragment, such as Fab and F(ab')2 fragments. This antibody can be produced according to commonly known methods (for example, Current Protocols in Molecular Biology, Edit. Ausubel et al. (1987), Publish. John Wiley and Sons. Section 11.12-11.13).

In the step of predicting whether chemotherapy with a combination drug of tegafur/gimeracil/oteracil potassium should be performed, it is predicted that when the expression level of thymidylate synthase gene is lower than a predetermined cut-off point, the patient is likely to sufficiently respond to the chemotherapy.

The cut-off point in the present invention is varied depending on conditions such as the subjects to be measured and the type of measurement methods, and is therefore required to be predetermined according to the conditions. Because the cut-off point is varied according to the subjects to be measured (the number, age, sex, body weight, health state, and disease state of patients), measurement methods (regarding which expression product, either gene or protein, is used for measurement), measurement conditions (for example, sequences of primers and probes in measuring gene expression products (mRNA), the type of label, the type and sensitivity of an antibody in the case where the expression product is a protein, and the like), statistical techniques, or other conditions, the present invention widely encompasses inventions using an arbitrary cut-off point that can be varied depending on these conditions, and is not limited to a particular value. Here, the cut-off point can be determined from the previously measured expression level of thymidylate synthase gene by using various statistical analysis techniques. Examples thereof include the average or median value of the expression level of thymidylate synthase gene in patients undergoing chemotherapy with a combination drug of tegafur/gimeracil/oteracil potassium; a value determined based on ROC (Receiver Operating Characteristic) analysis such that the sum of sensitivity and specificity is maximal from the relevance between the expression level of thymidylate synthase gene in patients undergoing chemotherapy with a combination drug of tegafur/gimeracil/oteracil potassium and with or without a certain therapeutic effect (tumor-shrinking effect, effect of prolonging progression-free survival, etc.) of the chemotherapy; a value in which P-value of the chi-square test is minimal or not higher than a certain level (for example, a value in which the P-value is not greater than 0.1, or not greater than 0.05) from the relevance between the expression level of thymidylate synthase gene in patients undergoing chemotherapy with a combination drug of tegafur/gimeracil/oteracil potassium and therapeutic effects (tumor-shrinking effect, effect of prolonging progression-free survival, etc.) of the chemotherapy; and a value in which P-value of the log-rank test is minimal or not higher than a certain level (for example, a value in which the P-value is not greater than 0.1, or not greater than 0.05) from the relevance between the expression level of thymidylate synthase gene in patients undergoing chemotherapy with a combination drug of tegafur/gimeracil/oteracil potassium, and the length of progression-free survival achieved with the chemotherapy.

As a result, the cut-off point (ratio to beta actin) for thymidylate synthase gene in this chemotherapy is, for example, in the real-time PCR method, preferably $1.55 \times 10^{-2}$ to $2.67 \times 10^{-2}$, more preferably $1.78 \times 10^{-2}$ to $2.50 \times 10^{-2}$, and particularly preferably $2.12 \times 10^{-2}$ to $2.50 \times 10^{-2}$.

EXAMPLES

Examples are given below to illustrate the present invention in more detail; however, it goes without saying that the present invention is not limited to these Examples.

Example 1

Measurement of Expression Level of Thymidylate Synthase Gene

A combination drug of tegafur/gimeracil/oteracil potassium (S-1) was orally administered to post-nephrectomy patients with metastatic renal cell carcinoma who did not respond to cytokine therapy or were judged to be ineligible for cytokine therapy, and a pharmacogenetic study was conducted as an additional study. A single dose of S-1 was the following initial standard dose per body surface area, and S-1 was orally administered twice a day, after breakfast and after dinner. The initial standard dose was 40 mg/dose for less than 1.25 m² of body surface area; 50 mg/dose for 1.25 m² or more to less than 1.50 m² of body surface area; and 60 mg/dose for 1.50 m² or more of body surface area. S-1 was orally administered for 28 consecutive days, followed by a 14-day withdrawal. This was regarded as one course, and administration was conducted for 2 or more courses, up to 4 courses.

A method for evaluating a therapeutic effect (antitumor effect) was according to General Rule for Clinical and Pathological Studies on Renal Cell Carcinoma (3rd ed.). The expression for response rating was as follows, in accordance with the Japan Society of Clinical Oncology criteria for evaluating the direct effect of chemotherapy for solid cancer.

1) Complete Response: CR

All measurable lesions, evaluable lesions, and secondary lesions due to tumor have disappeared, and no new lesions have emerged.

2) Partial Response: PR (i) The shrinkage rates for bidirectionally measurable lesions are 50% or more; and evaluable lesions and secondary lesions due to tumor have not aggravated; and no new lesions have emerged.

(ii) The shrinkage rates for unidirectionally measurable lesions as calculated using respective equations are 30% or more; and evaluable lesions and secondary lesions due to tumor have not aggravated; and no new lesions have emerged.

3) No Change: NC

The shrinkage rates for bidirectionally measurable lesions are less than 50%, or bidirectionally measurable lesions have increased in size by not greater than 25%; or the shrinkage rates for unidirectionally measurable lesions are less than 30%, or unidirectionally measurable lesions have increased in size by not greater than 25%; and secondary lesions due to tumor have not aggravated; and no new lesions have emerged.

4) Progressive Disease: PD

The sum of the products or diameters of measurable lesions have increased by 25% or more; or other lesions have aggravated; or new lesions have emerged.

Progression-free survival (PFS) was defined as the period from the first day of administration to the day when the disease progressed (day of the PD rating). When a subject died before disease progression, the death was handled as disease progression. In cases where no disease progression was observed, the last day of evaluation was used for the analysis.

The expression level of thymidylate synthase gene was quantified as a ratio to beta actin according to TaqMan (registered trademark) real time PCR using total RNA extracted from formalin-fixed paraffin-embedded sections of tumor tissues obtained at the time of nephrectomy, which were obtained prior to chemotherapy. Primers and probe of SEQ ID NOs: 1-3 below were used as those for measuring the expression level of thymidylate synthase gene. Furthermore, primers and probe of SEQ ID NOs: 4-6 below were used for measurement of the expression level of beta actin gene.

TABLE 1

| Gene name | Forward Primer | Reverse primer | TaqMan MGB probe |
|---|---|---|---|
| Thymidylate synthase | GAATCACATC GAGCCACTGA AA (SEQ ID NO: 1) | GAAGAATCCT GAGCTTTGGG AAA (SEQ ID NO: 2) | CAGCTTCAGC GAGAAC (SEQ ID NO: 3) |
| Beta actin | AAGGCCAACC GCGAGAAG (SEQ ID NO: 4) | ATAGCAACGT ACATGGCTGG G (SEQ ID NO: 5) | ACCCAGATCA TGTTT (SEQ ID NO: 6) |

In addition to the primers and probes described in Table 1 above, various forward primers, reverse primers, and probes can be designed based on the open reading frame of known thymidylate synthase gene sequence. The change in the sequences of primers or probes, type of label, etc., may slightly change the cut-off point; however, they have no substantial influence on the effect of the present invention, i.e., the effect that enables the prediction of whether a patient sufficiently responds to chemotherapy with a combination drug of tegafur/gimeracil/oteracil potassium.

Example 2

Calculation of Cut-Off Points

Cut-off points were determined from the expression level of thymidylate synthase gene in each patient, which was measured in Example 1, according to the following statistical analysis techniques.

(1) Using therapeutic effect data (efficacious: CR+PR, inefficacious: NC+PD), an optimal cut-off point in which the sum of sensitivity and specificity in ROC analysis was maximal was calculated. The calculated optimal cut-off point was $2.50 \times 10^{-2}$.

(2) A cut-off point in which P-value of the chi-square test was 5% or less was calculated using therapeutic effect data. The calculated cut-off point was $1.78 \times 10^{-2}$ to $2.67 \times 10^{-2}$.

(3) A cut-off point in which P-value of the log-rank test was minimal was calculated using progression-free survival data. The calculated cut-off point was $2.12 \times 10^{-2}$.

(4) A cut-off point in which P-value of the log-rank test was 5% or less was calculated using progression-free survival data. The calculated cut-off point was $1.55 \times 10^{-2}$ to $2.50 \times 10^{-2}$.

Example 3

Therapeutic Effects of S-1 Therapy in Patients Selected According to the Index, i.e., Thymidylate Synthase The cut-off point values calculated in Example 2 were used to divide the patients into two groups, low expression and high expression groups of thymidylate synthase (TS); and survival analysis was conducted. The results are shown in Tables 2 to 6.

TABLE 2

Cut-off point value: $1.55 \times 10^{-2}$ (lower limit of cut-off point in which P-value of the log-rank test is 5% or less)

| Subject | Number of cases | Response rate (%) | Median progression-free survival (month) |
|---|---|---|---|
| All | 31 | 32.3 | 9.2 |
| Low expression level of TS | 15 | 46.7 | >13.8* |
| High expression level of TS | 16 | 18.8 | 5.1 |

*Since median progression-free survival could not be calculated due to many censored cases, the minimum value was instead calculated with all censored cases handled as events.

TABLE 3

Cut-off point value: $1.78 \times 10^{-2}$ (median value)

| Subject | Number of cases | Response rate (%) | Median progression-free survival (month) |
|---|---|---|---|
| Low expression level of TS | 16 | 50.0 | >13.8* |
| High expression level of TS | 15 | 13.3 | 5.1 |

*Since median progression-free survival could not be calculated due to many censored cases, the minimum value was instead calculated with all censored cases handled as events.

TABLE 4

Cut-off point value: $2.12 \times 10^{-2}$ (P-value of the log-rank test is minimal)

| Subject | Number of cases | Response rate (%) | Median progression-free survival (month) |
|---|---|---|---|
| Low expression level of TS | 19 | 47.4 | >13.8* |
| High expression level of TS | 12 | 8.3 | 4.7 |

*Since median progression-free survival could not be calculated due to many censored cases, the minimum value was instead calculated with all censored cases handled as events.

TABLE 5

Cut-off point value: $2.50 \times 10^{-2}$ (optimal value in ROC analysis)

| Subject | Number of cases | Response rate (%) | Median progression-free survival (month) |
|---|---|---|---|
| Low expression level of TS | 22 | 45.5 | 18.8 |
| High expression level of TS | 9 | 0.0 | 5.1 |

TABLE 6

Cut-off point value: $2.67 \times 10^{-2}$ (upper limit of cut-off point in which P-value of the chi-square test is 5% or less)

| Subject | Number of cases | Response rate (%) | Median progression-free survival (month) |
|---|---|---|---|
| Low expression level of TS | 24 | 41.7 | 10.6 |
| High expression level of TS | 7 | 0.0 | 4.9 |

The patients with low expression levels of thymidylate synthase gene in tumor tissues responded highly to S-1 therapy as compared to the patients with high expression level of thymidylate synthase gene, with a significant difference in response rate and median progression-free survival. In addition, in these patients with low expression levels of thymidylate synthase gene in tumor tissues, the response rate and median progression-free survival were significantly excellent, even as compared to therapeutic effects (response rate: 10 to 36.5%, median progression-free survival: 5.5 to 8.7 months, N Engl J. Med. 2007; 356: 125-134, J Clin Oncol. 2006; 24: 16-24, JAMA. 2006; 295 (21): 2516-2524) achieved with the existing therapeutic agent for renal cell carcinoma (for example, molecular target drugs, such as sorafenib and sunitinib, etc.).

As described above, it is evident that selecting patients with renal cell carcinoma according to the expression level of thymidylate synthase gene makes it possible to ensure a high therapeutic effect of S-1 therapy.

The invention claimed is:

1. A therapeutic method for treating a patient for renal cell carcinoma comprising:
    measuring an expression level of thymidylate synthase gene in a cancer cell-containing biological sample obtained from a renal cell carcinoma patient; and
    administering a combination drug comprising tegafur/gimeracil/oteracil potassium to the patient when the patient has an expression level of thymidylate synthase gene that is equal to or less than a predetermined cut-off-point which is a value determined based on Receiver Operating Characteristic (ROC) analysis such that the sum of sensitivity and specificity is maximal from a ROC curve wherein the expression level of thymidylate synthase gene in patients undergoing chemotherapy with a combination drug of tegafur/gimeracil/oteracil potassium with an efficacious response rating is plotted against the expression level of thymidylate synthase gene in patients undergoing chemotherapy with a combination drug of tegafur/gimeracil/oteracil potassium with an inefficacious response rating.

2. The method of claim 1, wherein said combination drug comprises tegafur:gimeracil:oteracil potassium in a ratio of about 1:0.4:1.

3. The method of claim 1, wherein said predetermined cut-off point is determined from a previously measured expression level of thymidylate synthase gene.

4. The method of claim 1, wherein said predetermined cut-off point is a thymidylate synthase gene expression:beta actin ratio of $2.50 \times 10^{-2}$.

5. The method of claim 1, wherein therapeutic effect is evaluated according to a criteria wherein Complete Response (CR), Partial Response (PR), No Change (NC) and Progressive Disease (PD) are evaluated, and CR+PR constitutes an efficacious response rating and NC+PD constitutes an inefficacious response rating.

* * * * *